(12) United States Patent
Kamimoto et al.

(10) Patent No.: US 12,275,836 B2
(45) Date of Patent: Apr. 15, 2025

(54) SULFANYL SULFONIC ACID COMPOUND, VISCOELASTIC MODIFIER, RUBBER COMPOSITION, AND VULCANIZED RUBBER PRODUCTION METHOD

(71) Applicant: OTSUKA CHEMICAL CO., LTD., Osaka (JP)

(72) Inventors: Natsuyo Kamimoto, Ichihara (JP); Takeshi Hara, Ichihara (JP)

(73) Assignee: OTSUKA CHEMICAL CO., LTD., Osaka (JP)

( * ) Notice: Subject to any disclaimer, the term of this patent is extended or adjusted under 35 U.S.C. 154(b) by 349 days.

(21) Appl. No.: 17/912,380

(22) PCT Filed: Feb. 26, 2021

(86) PCT No.: PCT/JP2021/007421
§ 371 (c)(1),
(2) Date: Sep. 16, 2022

(87) PCT Pub. No.: WO2021/199818
PCT Pub. Date: Oct. 7, 2021

(65) Prior Publication Data
US 2023/0144404 A1    May 11, 2023

(30) Foreign Application Priority Data

Mar. 30, 2020  (JP) .................. 2020-060407

(51) Int. Cl.
*C08K 5/42*     (2006.01)
*C07C 323/66*   (2006.01)
(Continued)

(52) U.S. Cl.
CPC .............. *C08K 5/42* (2013.01); *C07C 323/66* (2013.01); *C08C 1/02* (2013.01); *C08K 3/06* (2013.01); *C08L 7/00* (2013.01)

(58) Field of Classification Search
CPC .......... C08K 5/42; C08K 3/06; C07C 323/66; C08C 1/02; C08L 7/00
See application file for complete search history.

(56) References Cited

U.S. PATENT DOCUMENTS

2012/0101219 A1\* 4/2012 Ozturk ..................... C08K 5/42
                                                        524/575.5
2014/0065337 A1\* 3/2014 Shiratani ............... C07C 381/02
                                                        524/157

FOREIGN PATENT DOCUMENTS

JP    2011-202137 A    10/2011
JP    2011-202138 A    10/2011
(Continued)

OTHER PUBLICATIONS

International Searching Authority, "International Search Report," issued in connection with International Patent Application No. PCT/JP2021/007421, dated Apr. 20, 2021.
(Continued)

*Primary Examiner* — John E Uselding
(74) *Attorney, Agent, or Firm* — Foley & Lardner LLP

(57) ABSTRACT

Disclosed is a sulfanyl sulfonic acid compound represented by the following formula (1) or a metal salt thereof. In the formula, m represents an integer of 2 to 7, n represents an integer of 3 to 10, and $R^1$ and $R^2$ each independently represent a hydrogen atom or an alkyl group.

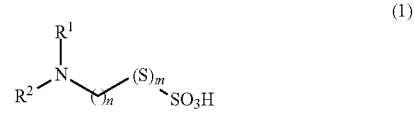

(1)

4 Claims, 1 Drawing Sheet

(51) Int. Cl.
*C08C 1/02* (2006.01)
*C08K 3/06* (2006.01)
*C08L 7/00* (2006.01)

(56) References Cited

FOREIGN PATENT DOCUMENTS

| | | |
|---|---|---|
| JP | 2014-221863 A | 11/2014 |
| JP | 2017-048351 A | 3/2017 |

OTHER PUBLICATIONS

International Searching Authority, "Written Opinion," issued in connection with International Patent Application No. PCT/JP2021/007421, dated Apr. 20, 2021.

\* cited by examiner

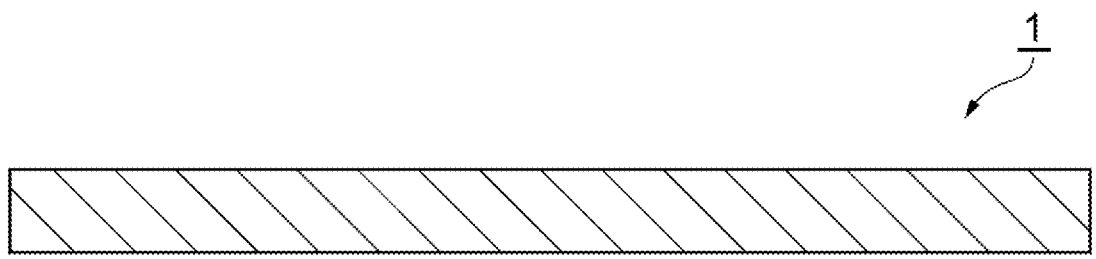

SULFANYL SULFONIC ACID COMPOUND, VISCOELASTIC MODIFIER, RUBBER COMPOSITION, AND VULCANIZED RUBBER PRODUCTION METHOD

CROSS-REFERENCE TO RELATED APPLICATIONS

The present application claims priority under 37 U.S.C. § 371 to International Patent Application No. PCT/JP2021/007421, filed Feb. 26, 2021, which claims priority to and the benefit of Japanese Patent Application No. 2020-060407, filed on Mar. 30, 2020. The contents of these applications are hereby incorporated by reference in their entireties.

TECHNICAL FIELD

The present invention relates to a sulfanyl sulfonic acid compound, a viscoelastic modifier, a rubber composition, and a method for producing a vulcanized rubber.

BACKGROUND ART

Vulcanized rubber is widely used in automotive tires. For the purpose of improving fuel consumption of automobiles, etc., investigated are methods for improving viscoelastic properties of vulcanized rubber for automotive tires (e.g., Patent Literatures 1 and 2).

CITATION LIST

Patent Literature

Patent Literature 1: Japanese Patent Laid-Open No. 2011-202137
Patent Literature 2: Japanese Patent Laid-Open No. 2011-202138

SUMMARY OF INVENTION

Technical Problem

One aspect of the present invention provides a new compound which can modify viscoelasticity of a vulcanized rubber at a high temperature.

Solution to Problem

One aspect of the present invention provides a sulfanyl sulfonic acid compound represented by the following formula (1) or a metal salt thereof:

[Formula 1]

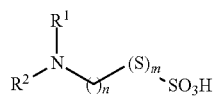

(1)

wherein m represents an integer of 2 to 7, n represents an integer of 3 to 10, and $R^1$ and $R^2$ each independently represent a hydrogen atom or an alkyl group.

Another aspect of the present invention provides a viscoelastic modifier for vulcanized rubber comprising at least one of the above sulfanyl sulfonic acid compound or the metal salt thereof. In other words, another aspect of the present invention provides a viscoelastic modifier for vulcanized rubber comprising the above sulfanyl sulfonic acid compound and/or the metal salt thereof.

Yet another aspect of the present invention provides a rubber composition comprising a rubber component, a sulfur component, and at least one of the above sulfanyl sulfonic acid compound or the metal salt thereof. In other words, yet another aspect of the present invention provides a rubber composition comprising a rubber component, a sulfur component, and the above sulfanyl sulfonic acid compound and/or the metal salt thereof.

Yet another aspect of the present invention provides a method for producing a vulcanized rubber comprising heat-treating the above rubber composition.

Advantageous Effects of Invention

According to one aspect of the present invention, provided is a new compound which can modify viscoelasticity of a vulcanized rubber at a high temperature of about 60° C. According to another aspect of the present invention, provided is a vulcanized rubber of which tan δ at a high temperature of about 60° C. is reduced.

BRIEF DESCRIPTION OF DRAWING

The FIGURE is a schematic cross section showing one embodiment of a vulcanized rubber.

DESCRIPTION OF EMBODIMENTS

Hereinafter, some embodiments of the present invention will be described in detail. However, the present invention is not limited to the following embodiments.

A sulfanyl sulfonic acid compound according to one embodiment is a compound represented by the following formula (1):

[Formula 2]

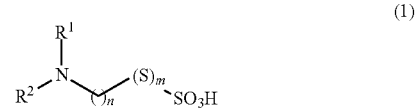

(1)

In the formula (1), m represents an integer of 2 to 7, n represents an integer of 3 to 10, and $R^1$ and $R^2$ each independently represent a hydrogen atom or an alkyl group. m may be 2 to 6, 2 to 5, 2 to 4, 2 to 3, or 2. n may be 2 to 6, 2 to 5, 2 to 4, or 3. The alkyl group as $R^1$ or $R^2$ may be an alkyl group having 1 to 6 carbon atoms.

The sulfanyl sulfonic acid compound may be a metal salt of the compound represented by the formula (1). The metal salt may be lithium salts, sodium salts, potassium salts, cesium salts, cobalt salts, copper salts, or zinc salts, and may be lithium salts, sodium salts, or potassium salts.

The sulfanyl sulfonic acid compound of the formula (1) can be synthesized by a method comprising reacting, e.g., S-alkylthiosulfuric acid (e.g., S-(3-aminopropyl)thiosulfuric acid) with sulfur. Reaction conditions may be a nitrogen atmosphere, a light-shielding condition, or a combination thereof. With respect to an amount of the S-alkylthiosulfuric acid, an amount of the sulfur may be 0.5 to 2 equivalent weight, or 1.2 equivalent weight. The reaction can be performed in a solvent (e.g., dimethylformamide). A reaction time is not limited, and may be 1 to 12 hours. A reaction temperature is not limited, and may be, e.g., 60 to 110° C. The S-alkylthiosulfuric acid may be obtained as commercially available products or synthesized by a method known to one skilled in the art.

The sulfanyl sulfonic acid compound of the formula (1), the metal salt thereof, or a combination thereof can be used as a viscoelastic modifier to modify viscoelasticity of a vulcanized rubber. This viscoelastic modifier can reduce tan δ of a vulcanized rubber, e.g., at a high temperature of about 60° C.

A rubber composition according to one embodiment comprises a rubber component, a sulfur component, and the sulfanyl sulfonic acid compound of the formula (1) and/or the metal salt thereof.

Examples of the rubber component may include at least one selected from the group consisting of a natural rubber, a modified natural rubber (e.g., epoxidized natural rubber, deproteinized natural rubber), a polyisoprene rubber (IR), a styrene-butadiene copolymer rubber (SBR), a polybutadiene rubber (BR), an acrylonitrile-butadiene copolymer rubber (NBR), an isoprene-isobutylene copolymer rubber (IIR), an ethylene-propylene-diene copolymer rubber (EPDM), and a halogenated butyl rubber (HR). The rubber component may include a highly unsaturated rubber such as a natural rubber, a styrene-butadiene copolymer rubber, or a polybutadiene rubber, and may include a natural rubber. The rubber component may include a combination of a natural rubber and a styrene-butadiene copolymer rubber or a polybutadiene rubber.

The sulfur component may be anything that can vulcanize the rubber composition, and examples may include at least one selected from powdered sulfur, precipitated sulfur, colloidal sulfur, insoluble sulfur, and highly dispersible sulfur. Here, the sulfur component is a sulfur containing component except for the sulfanyl sulfonic acid compound of the formula (1) and the metal salt thereof, and an accelerator. A content of the sulfur component may be 0.3 to 5 parts by mass, or 0.5 to 3 parts by mass, with respect to 100 parts by mass of the rubber component.

A content of the sulfanyl sulfonic acid compound of the formula (1) and/or the metal salt thereof may be, with respect to 100 parts by mass of the rubber component, 5 parts by mass or less, or 3 parts by mass or less, and may be 0.03 parts by mass or more, 0.04 parts by mass or more, 0.05 parts by mass or more, 0.06 parts by mass or more, 0.07 parts by mass or more, 0.08 parts by mass or more, 0.09 parts by mass or more, or 0.1 parts by mass or more. The content of the sulfanyl sulfonic acid compound of the formula (1) and/or the metal salt thereof may be, with respect to 100 parts by mass of the rubber component, 5 parts by mass or less and 0.03 parts by mass or more, 0.04 parts by mass or more, 0.05 parts by mass or more, 0.06 parts by mass or more, 0.07 parts by mass or more, 0.08 parts by mass or more, 0.09 parts by mass or more, or 0.1 parts by mass or more, and may be 3 parts by mass or less and 0.03 parts by mass or more, 0.04 parts by mass or more, 0.05 parts by mass or more, 0.06 parts by mass or more, 0.07 parts by mass or more, 0.08 parts by mass or more, 0.09 parts by mass or more, or 0.1 parts by mass or more.

The rubber composition may include other components as required. Examples of other components include a filler (e.g., carbon black, silica), an accelerator, zinc oxide, an antioxidant, an oil, and a fatty acid. A content of the filler may be 35 to 150 parts by mass with respect to 100 parts by mass of the rubber component.

The rubber composition can be obtained by a method comprising a step of mixing a mixture containing, e.g., the rubber component, the sulfanyl sulfonic acid compound of the formula (1) and/or the metal salt thereof, and the filler added as required, to obtain a compound, and a step of mixing the compound with additional components containing the sulfur component, to obtain the rubber composition.

By a method comprising heat-treating the rubber composition, a vulcanized rubber containing the rubber component vulcanized can be produced. Before heat-treating the rubber composition, the rubber composition may be formed into a predetermined shape, or integrated with other members. A heat-treating temperature for vulcanization may be, e.g., 120 to 180° C. The heat-treatment can be performed at normal pressure or under pressure. The FIGURE is a cross section showing one embodiment of a vulcanized rubber. The vulcanized rubber shown in the FIGURE is a sheet-like formed product. However, the shape of the vulcanized rubber is not limited to this shape, and can have an arbitrary shape which is required for the application.

The vulcanized rubber can be used as, e.g., rubber members (a belt, a carcass, an inner liner, a side wall, a tread, etc.) constituting automotive tires.

EXAMPLES

Hereinafter, the present invention will be specifically explained with examples. However, the present invention is not limited to these examples.

1. Synthesis of Sulfanyl Sulfonic Acid Compound [(3-aminopropyl)disulfanyl]sulfonic acid

[Formula 3]

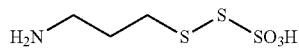

Under the conditions of a nitrogen atmosphere and a light-shielding, S-(3-aminopropyl)thiosulfuric acid (50 g, 292 mmol) and sulfur (manufactured by FUJIFILM Wako Pure Chemical Corporation) (11.2 g, 349 mmol, 1.2 equivalent weight) were stirred in dimethylformamide of 500 mL for 5 hours with heating to 90° C., to proceed with a reaction. Next, by vacuum concentration, dimethylformamide was distilled off. A crude product of residue was purified by reversed-phase chromatography (Wakogel 50C18 (product name), developing solvent: trifluoroacetic acid/water/acetonitrile=0.05/99/1), to obtain 13.6 g of [(3-aminopropyl)disulfanyl]sulfonic acid of interest. A structure of the product was identified by $^1$H-NMR and $^{13}$C-NMR. A melting point of the product was 192° C.

$^1$H-NMR (400 MHz, DMSO-D$_6$) $\delta_{ppm}$: 7.62 (2H, br), 2.91 (4H, m), 1.95 (2H, m), $^{13}$C-NMR (100 MHz, D$_{2O}$) $\delta_{ppm}$: 49.5, 38.6, 35.5, 26.4.

2. Preparation and Evaluation of Rubber Composition

Example 1

<1st Mixing: Mixing by Labo Plastomill>

Using a Labo Plastomill (manufactured by Toyo Seiki Seisaku-sho, Ltd., capacity: 600 mL), 100 parts by mass of a natural rubber (RSS #1), 45 parts by mass of HAF carbon black (manufactured by Asahi Carbon Co., Ltd., product name "Asahi #70"), 3 parts by mass of stearic acid, 5 parts by mass of zinc oxide, 1 part by mass of an antioxidant (N-phenyl-N'-1,3-dimethylbutyl-p-phenylenediamine (6 PPD), product name "Antigen® 6C" manufactured by Sumitomo Chemical Co., Ltd.), and 0.5 parts by mass of [(3-aminopropyl)disulfanyl]sulfonic acid were mixed to obtain a compound. A mixing time was 5 minutes after adding each component, and a rotation speed of a mixer was 50 rpm. A temperature of the compound in the Labo Plastomill was 150 to 180° C.

<2nd Mixing: Mixing by Open Roll Machine>

The compound containing 100 parts by mass of the natural rubber obtained in the 1st Mixing, 1 part by mass of an accelerator (N-cyclohexyl-2-benzothiazolylsulfenamide (CBS)), and 2 parts by mass of powdered sulfur (manufactured by Hosoi Chemical Industry Co., Ltd., "Fine Powder Sulfur") were mixed by an open roll machine in which a roll temperature was set to 60° C., to obtain a sheet-like rubber composition.

<Vulcanization>

The rubber composition obtained in the 2nd Mixing was heat-treated at 145° C. for 30 minutes to obtain a vulcanized rubber.

Examples 2, 3 and Comparative Example 1

Rubber compositions and vulcanized rubbers of Examples 2, 3 and Comparative Example 1 were obtained in the same manner as in Example 1 except that the amounts of the sulfanyl sulfonic acid compound ([(3-aminopropyl)disulfanyl]sulfonic acid) were changed to the amounts (parts by mass) shown in Table 1.

Viscoelasticity of Vulcanized Rubber

Using a viscoelasticity analyzer manufactured by Ueshima Seisakusho Co., Ltd., tan δ of the vulcanized rubber at 60° C. was measured under the following conditions.

Temperature: 60° C., Initial Strain: 10%, Dynamic Strain: 2.5%, Frequency: 10 Hz Table 1 shows a decrease percentage of a tan δ value of each Example with respect to the tan δ value of Comparative Example 1. For example, "30%" of Example 1 means that the tan δ value at 60° C. was decreased by 30% compared with that of the vulcanized rubber of Comparative Example 1. It was confirmed that each of the vulcanized rubbers obtained in Examples 1 to 3 had improved viscoelastic properties.

TABLE 1

|  |  | Comparative Example 1 | Example 1 | Example 2 | Example 3 |
|---|---|---|---|---|---|
| 1st Mixing | Natural Rubber | 100 | 100 | 100 | 100 |
|  | Carbon Black | 45 | 45 | 45 | 45 |
|  | Stearic Acid | 3 | 3 | 3 | 3 |
|  | Zinc Oxide | 5 | 5 | 5 | 5 |
|  | Antioxidant | 1 | 1 | 1 | 1 |
|  | Sulfanyl Sulfonic Acid Compound | 0 | 0.5 | 1 | 2 |
|  | Subtotal | 154 | 154.5 | 155 | 156 |
| 2nd Mixing | Powdered Sulfur | 2 | 2 | 2 | 2 |
|  | CBS | 1 | 1 | 1 | 1 |
|  | Total | 157 | 157.5 | 158 | 159 |
| Viscoelasticity | tanδ/60° C. (Decrease Percentage with respect to Comparative Example 1) | — | 30% | 32% | 35% |

The invention claimed is:

1. A sulfanyl sulfonic acid compound represented by the following formula (1) or a metal salt thereof:

[Formula 1]

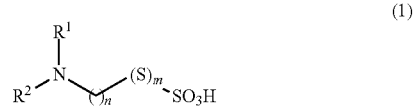

wherein m represents an integer of 2 to 7, n represents an integer of 3 to 10, and $R^1$ and $R^2$ each independently represent a hydrogen atom or an alkyl group.

2. A viscoelastic modifier for vulcanized rubber comprising at least one of the sulfanyl sulfonic acid compound or the metal salt thereof according to claim 1.

3. A rubber composition comprising a rubber component, a sulfur component, and at least one of the sulfanyl sulfonic acid compound or the metal salt thereof according to claim 1.

4. A method for producing a vulcanized rubber comprising heat-treating the rubber composition according to claim 3.

* * * * *